United States Patent

Horton et al.

Patent Number: 4,870,058
Date of Patent: Sep. 26, 1989

[54] 14-ACYLOXY-2'-HALO-ANTHRACYCLINE ANTI-CANCER ANTIBIOTICS

[75] Inventors: Derek Horton; Waldemar Priebe, both of Columbus, Ohio

[73] Assignee: Ohio State University Research Foundation, Columbus, Ohio

[21] Appl. No.: 151,755

[22] Filed: Feb. 3, 1988

Related U.S. Application Data

[63] Continuation of Ser. No. 42,624, Apr. 23, 1987, Pat. No. 4,772,624, which is a continuation of Ser. No. 623,741, Jun. 22, 1984, abandoned, which is a continuation-in-part of Ser. No. 450,863, Dec. 20, 1982, abandoned.

[51] Int. Cl.$^4$ .................. A61K 31/70; C07H 15/24
[52] U.S. Cl. ............................. 514/34; 536/6.4
[58] Field of Search .......................... 536/6.4; 514/34

[56] References Cited

U.S. PATENT DOCUMENTS

| | | | |
|---|---|---|---|
| 4,166,848 | 9/1979 | Bernardi et al. | 536/6.4 |
| 4,537,882 | 8/1985 | Hordon et al. | 536/6.4 |

Primary Examiner—Herbert J. Lilling
Assistant Examiner—Elli Peselev
Attorney, Agent, or Firm—Smith & Schnacke

[57] ABSTRACT

Compounds of the formula (I) and pharmaceutical preparations containing the same are disclosed

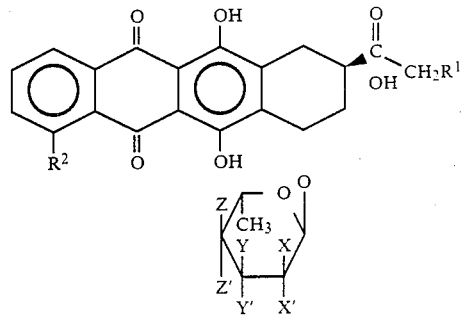

wherein $R^1$ is —OOCR$^3$ or —OOC(CH$_2$)$_n$COOR$^4$; $R^2$ is hydrogen, hydroxy or methoxy; one of X and X' is a halogen atom selected from the group consisting of fluorine, chlorine, bromine and iodine and the other is hydrogen; one of Y and Y' is hydrogen and the other is selected from the group consisting of hydrogen, hydroxy and acyloxy; one of Z and Z' is hydrogen and the other is selected from the group consisting of hydrogen, hydroxy and acyloxy; $R^3$ is an alkyl group containing 1 to 8 carbon atoms; $R^4$ is a hydrogen atom, a metal atom, or an alkyl group containing 1 to 4 carbon atoms; and n is an integer of 0 to 6. These compounds are active in the inhibition of malignant diseases.

6 Claims, No Drawings

14-ACYLOXY-2'-HALO-ANTHRACYCLINE ANTI-CANCER ANTIBIOTICS

This is a continuation of application Ser. No. 042,624, filed Apr. 23, 1987, now U.S. Pat. No. 4,772,620, which is a continuation of Ser. No. 623,741, filed June 22, 1984, which in turn is a continuation-in-part of Ser. No. 450,863, filed Dec. 20, 1982, both abandoned.

BACKGROUND OF THE INVENTION

Anthracyline antibiotics including doxorubicin, daunorubicin, and carminomycin are important chemotherapeutic agents in the treatment of a broad spectrum of neoplastic conditions including acute myeloblastic and lymphoblastic leukemias. Doxorubicin (also known as Adriamycin) is the subject of U.S. Pat. No. 3,590,028 and is a prescribed antineoplastic agent used in a number of chemotherapeutic treatments.

Certain undesirable side effects have limited the usefulness of known anthracyline antibiotics. One of their more serious side effects, however, is their cardiotoxicity which severely restricts the dosages and the frequency with which they can be administered and, in turn, limits their overall effectiveness as an antibiotic. Many of the other side effects which accompany the administration of these agents can be managed by administering other pharmaceutical agents in combination with them, however, the cardiopathic effects are not easily controlled or reversed.

In view of the proven effectiveness of known anthracyclines in the treatment of cancer, efforts have been undertaken to develop less toxic derivatives which can be administered in high, more effective dosages with greater frequency. The compounds disclosed in U.S. Pat. No. 4,201,773 to Horton et al., are among anthracyline derivatives that have been proposed to have better therapeutic ratios than their naturally occurring counterparts. These compounds are derivatives of Andriamycin, daunomycin, and 4-demethoxydaunomycin in which the 3'amino group in the sugar moietry is substituted with a hydroxy group. Horton and Priebe also disclose a number of 2'-halo derivatives of Andriamycin, daunomycin and 4-demethoxydaunomycin in their U.S. Pat. No. 4,427,664.

One of the disadvantages of the aforementioned compounds is that they have relatively low solubility in water. This limits their usefulness and effectiveness because it often necessitates that they be administered in large volumes of infusate over a period of hours.

Furthermore, in view of their low water solubility, the compounds are difficult to administer in amounts which would be effective in the treatment of some cancers.

Thus, there is a need for less toxic anthracyline antibiotics which are water soluble and readily absorbed into the blood stream.

SUMMARY OF THE INVENTION

The present invention relates to a novel anthracyline antibiotic which is represented by the formula (I)

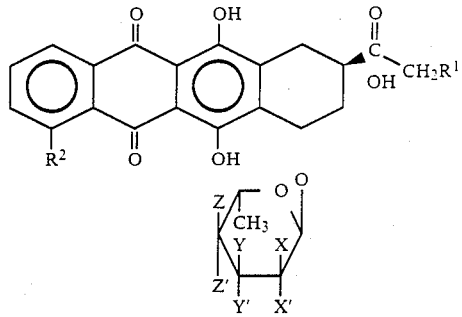

wherein $R^1$ is —))$CR^3$ or —$OOC(CH_2)_nCOOR^4$; $R^2$ is hydrogen, hydroxy or methoxy; one of X and X' is a halogen atom selected from the group consisting of fluorine, chlorine, bromine, and iodine and the other is hydrogen; one of Y and Y' is hydrogen and the other is selected from the group consisting of hydrogen, hydroxy and acyloxy; one of Z and Z' is hydrogen and the other is selected from the group consisting of hydrogen, hydroxy and acyloxy; $R^3$ is an alkyl group containing 1 to 8 carbon atoms; $R^4$ is a hydrogen or metal atom (for example an alkali metal atom such as Na, k, and the like), or an alkyl group containing 1 to 4 carbon atoms, and n is an integer of 0 to 6.

The present invention also provides pharmaceutical preparations containing the aforesaid compounds in suitable carriers and in therapeutically effective amounts.

In a more particular embodiment, the present invention provides compounds of the formula (I) wherein $R^2$ is hydrogen, hydroxy or methoxy; one of X and X' (preferably X') is bromine or iodine; one of Y and Y' (preferably Y') is acetoxy or hydroxy; one of Z and Z' is acetoxy or hydroxy and $R^1$ is represented by the formula —$OOCR^3$ or —$OOC(CH_2)_nCOOR^4$ wherein $R^4$ is a hydrogen or metal atom, the balance of the substitutes being defined as above.

In a still more particular embodiment, the present invention provides compounds of the formula (I) wherein $R^2$ is methoxy; X' is iodine; Y' is acetoxy or hydroxy, Z or Z' is acetoxy or hydroxy and $R^1$ is hemiglutaryloxy, hemiadipoyloxy, or acetoxy.

DETAILED DESCRIPTION OF THE INVENTION

The compounds of the present invention are 14-acyloxy-3'adeamino-2'-halo derivatives of the antibiotics doxorubicin, carminomycin, and 4-demethoxydaunomycin.

The anthracycline derivatives of the present invention are glycosides made up of an anthracylcinone substituted with an acyloxy group at C-14 which is coupled at C-7 to a 2,6-dideoxy-2-halo-hexopyranose sugar. In general, these compounds are prepared by two alternative routes:

(1) By reacting 1,5-anhydro-2,6-dideoxyhex-1-enitols (6-deoxy-glycals) with an equimolar amount of a 14-O-acyl-aglycon in the presence of N-halogeno-succinimide to form the 2-halo glycoside; or by reacting the appropriate glycals with halogen and then coupling them with anthracyclinones by using known coupling reagents (for example silver trifluoromethanesulfonate).

(b 2) By reacting the sugar with daunomycinone or 4-demethoxydaunomycinone under the above described conditions followed by functionalization of position 14 by halogenation (for example, bromination in an inert solvent) and reacting the product with a sodium or potassium salt of a fatty acid of the formula $R^3COOH$ where $R^3$ is defined as above analogous to the teachings in U.S. Pat. No. 3,803,124. Where $R^1$ is a dicarboxylic acid moiety, the monosodium salt of the dicarboxylic acid may be used as above. The 14-O-hemiglutarate and the 14-O-hemiadipate derivatives of the present invention can be prepared by analogy to the teachings in U.S. Pat. No. 4,299,822.

The compounds of the present invention are preferably prepared from 1,6-anhydro-3,4-di-O-acetyl-2,6-dideoxy-hex-1-enitols such as 3,4-di-O-acetyl-L-fucal or 3,4-di-O-acetyl-L rhamnal. These sugars can be prepared as described in B. Iselin and T. Reichstein, *Helv. Chim. Acta*, 27,1146, 1200 (1944). The aglycon is usually reacted with 3,4-di-O-acetyl-L-rhamnal or 3,4,-di-O-acetyl-L-fucal in an anhydrous mixture of acetonitrile and tetrahydrofuran followed by the addition of a halogenating agent such as N-iodosuccinimide or N-bromosuccinimide. The halogenating agent is generally used in a stoichiometric excess, e.g., 1.5 to 3 times the amount of the aglycon on a molar basis.

The synthesis of the compounds of the present invention will now be illustrated in more detail by the following examples:

EXAMPLE 1

Preparation of 14-O-acetyl-7-0-(3,4di-O-acetyl2,6-dideoxy-2-iodo-α-L-manno-hexopyranosyl) adriamycinone.

0.92 mmol (198 mg) of 3,4-di-O-acetyl-L-rhamnal and 0.52 mmol (239 mg) of 14-O acetyladriamycinone (prepared in accordance with U.S. Pat. No. 3,803,124) were added to a mixture of dry acetonitrile (14ml) and tetrahydrofuran (7 ml). The reaction mixture was flushed with dry argon and cooled to 0° C. while N-iodosuccinimide in an amount of 1.52 mmol (343 mg) was added thereto. The mixture was stirred at room temperature for 44 hours.

Thin layer chromatography (3:1 toluene-acetone) was performed on precoated plastic sheets (0.2 mm) coated with silica gel 60 F-254 (E. Merck, Darmstadt, G.F.R.) and showed the presence of one major and one less-polar minor product. Traces of substrate were still present. The mixture was diluted with dichloromethane (100 ml) and shaken twice with 10% aqueous sodium thiosulfate (50 ml), and washed twice with an excess of water. The organic layer was dried with $MgSO_4$. Filtration and evaporation of the solvent gave a thick, dark, red syrup which was dissolved in chloroform and evaporated onto silica gel (3 g). The red powder thus obtained was placed on a column of silica gel 60 (230-400 mesh) (E. Merck, Darmstadt, G.F.R.). (30 g in 2:1 hexane-ethyl acetate). The column was eluted first with 2:1 hexane-ethyl acetate (200 ml) and then with 8:1 toluene-acetone. Two fractions were obtained. The more-polar one was isolated and fully characterized after crystalization from acetone, ethyl ether, and hexane, m.p. 130°–135° C.; $[\alpha]_D^{21}$ +94° (c 0.02, chloroform); $\nu^{Kbr}{}_{max}$ 3380 (OH), 1745–1720 (C=O), 1610 and 1575 $cm^{-1}$ (chelated quinone); $^1$H-n.m.r. (CDCl$_3$, 200 MHz): ≃ 13.95, 13.15 (s, 1H, HO-6, HO-11), 8.00 (dd, 1H, $J_{1,2}$ 7.7, $J_{1,3}$ 1.1 Hz, H-1), 7.77 (apparent t, 1H, H-2), 7.39 (dd, 1H, $J_{2,3}$ 8.5 Hz H-3), 5.78 (bs, 1H, H-1'), 5.34 (d, 1H, $J_{14A,14B}$ 18.4 Hz, H-14A), 5.26 (m, 1H, H-7), 5.18 (t, 1H, $H_{3',4'}=J_{4',5'}$ 9.5 Hz, H-4'), 512 (d, 1H, H-14B), 4.59 (dd, 1H, $J_{1',2'}$ 1.5, $J_{2',3'}$ 4.4 Hz, H-2'), 4.33 (dd, 1H, H-3'), 4.16 (s, 1H, HO-9), 4.10 (dq, 1H, H-5'), 4.08 (s, 3H, OMe), 3.27 (dd, 1H, $J_{8e,10e}$ 1.5 Hz, H-10e), 2.93 (d, 1H, $J_{10e,10ax}$ 19.1 Hz, H-10ax), 2.45 (bd, 1H, $J_{8e,8ax}$ 15.1 Hz, H-8e), 2.21-2.07 (m, 1H, H-8ax), 2.21, 2.07, 2.04 (s, 3H, OAc), 1.31 (d, 3H $J_{5',6'}$ 6.25, H-6'); $^{13}$C-n.m.r. (CDCl$_3$, 50 MHz): ≃ 206.6 (C-13), 187.4, 187.1 (C-5, C-12), 170.6, 169.9 (C=O), 161.4 (C-4), 156.3, 155.8 (C-6, C-11), 135.9 (C-2), 135.7, 134.0, 132.9 (C-6a, C-10a, C-12), 121.1 (C-4a), 120.0 (C-1), 118.7 (C-3), 111.9, 111.8 (C-5a, C-11a), 104.7 (C-1'), 76.8 (C-9, signal strongly overlap with CDCl$_3$ signals), 72.4 (C-4'), 70.6 (C-7), 69.1 (C-3'), 68.5 (C-5'), 65.9 (C-14), 56.7 (OMe), 35.5 (C-8), 33.6 (C-10), 29.0 (C-2'), 20.7, 20.6, 20.3 (OAc), 17.3 (C-6').

Anal. Calc. for $C_{33}H_{33}IO_{15}$ (796.526); C, 49.76; H, 4.18; I, 15.93. Found: C, 49.65; H, 4.36.

EXAMPLE 2

Preparation of 7-0-(3,4di-O-acetyl-2,6-dideoxy-2-iodo-α-L-manno-hexopyranosyl)-14-0-(5-carboxypentanoyl) adriamycinone.

1.385 mmol (1.023 g) of 7-0-(3,4di-0-acetyl-2,6-dideoxy-2-iodo-α-L-manno-hexopyranosyl) daunamycinone was dissolved in chloroform. Then 1.75 g of bromine in 10 ml chloroform was added. The reaction was monitored by TLC (toluene:acetone 4:1), and after 6 hours no substrate was present. The sample was concentrated on the rotary evaporator and evaporated twice with chloroform. Then the sample was crystallized from chloroform-ethyl ether-hexane to provide 842 mg of 14-bromo-7-0-(3,4-di-0-acetyl-2,6-dideoxy-2-iodi-α-L-manno-hexopyranosyl) daunomycinone. 289.2 mg. (0.354 mmol) of the 14-bromo compound was dissolved in 2,4-pentanedione (60 ml), then 1.2 g of monosodium adipate was added and was refluxed for 40 min. After the reaction mixture reached room temperature methylene chloride (300 ml) was added and the solution was filtered, washed several times with water and dried over magnesium sulfate. Chromatography afforded 130 mgs. (41.6%) of red foam which was crystallized from chloroform-ethyl ether-hexane. Yield: 74 mg (23.7%). m.p. 125°–130°, $[\alpha]^{26}$+94° (c 0.02, chloroform); $\nu_{max}^{KBr}$ 3470 (OH), 1735 (bs C+0), 1618, and 1577 $cm^{-1}$ (chelated quinone): $^1$H-n.m.r. (CDCl$_3$, 300 MHz), δ 13.92, 13.10 (s, $^1$H, HO-6, 11), 7.97 (d, 1H, $J_{1,2}$ 7.4 Hz, H-1), 7.76 (app. t, 1H, H-2) 7.37 (d, 1H, $J_{2,3}$ 8.1 Hz, H-3), 5.78 (s, 1H, H-1'), 5.32 (d, 1H, $J_{14A,14B}$ 18.2 Hz, H-14A), 5.28 (m, 1H, H-7), 5.18 (t, 1H, $J_{3',4'}=J_{4',5'}$ 9.4 Hz, H-4'), 5.15 (d, 1H, H-14B), 4.59 (d, 1H, $J_{2',3'}$ 4.3 Hz, H-2'), 4.34 (dd, 1H, H-3'), 4.08 (m, H-5, OCH$_3$), 3.31 (dd, 1H, $J_{8e,10e}$ 1.1 Hz, H-10e), 2.99 (d, 1H, $J_{10e,10ax'}$, 19.0 Hz, H-10ax), 2.46 (m, 5H, CH$_2$, H-8e), 2.19-2.06 (m, 1H, H-8ax), 2.07, 2.04 (s, 3H, OAc), 1.76 (m, 4H, CH$_2$), 1.31 (d, 3H, $J_{5',6'}$ 6.3 Hz, H-6'), 13C-n.m.r. (CDCl$_3$, 50 MHz); δ 206.5 (C-13), 187.1, 186.9 (C-5, C-12), 175.1, 172.9, 169.9, 169.8 (C=O), 161.3 (C-4), 156.2, 155.7 (C-6, C-11), 135.9 (C-2), 135.6, 134-0, 132.9 (C-6a, 10a, 12a), 120.9 (C-4a), 119.9 (C-1), 118.7 (C-3) 111.8, 111.7 (C-5a, 11a), 104.6 (C-1'), 77.0 (C-9, overlap with CDCl$_3$), 72.5 (C-4'), 70.6 (C-7), 69.1 (C-3'), 68.5 (C-5'), 65.8 (C-14), 56.6 (OMe), 35.4 (C-8), 33.5, 33.4, 33.3 (C-10, CH$_2$) 29.1 (C-2'), 24.1, 23.9 (CH$_2$), 20.7, 20.6 (OAc), 17.3 (C-6').

Therapeutic compositions containing the novel compounds of the present invention as active agents can be prepared by dispersing or dissolving the compound in any pharmaceutically acceptable non-toxic carrier suitable for the desired mode of administration. Therapeutic compositions of the present invention may be administered parenterally by intravenous, intraperitoneal, or other conventional injection or orally in some cases. Preferably, the carrier is an aqueous medium buffered to pH 7.2–7.5, the physiological range. Any suitable conventional buffer can be used such as tris phosphates, bicarbonates or citrates. If desired, saline solution can be used, with pH adjustment and buffering. Optimal dosages may vary over a broad range from approximately 0.1 to 10 mg/kg of body weight depending upon the particular compound employed.

As demonstrated in the following biological examples, the compounds of the present invention are useful in inhibiting malignant diseases such as murine P-388 and murine L-1210 leukemias and B-16 melanoma.

BIOLOGICAL EXAMPLE 1

The test compounds listed below were administered to mice innoculated by intraperitoneal injection with P-388 or L-1210 leukemia cells of B16 Melanoma cells. A single dose of the test compounds was administered on the days indicated beginning on day 1, 24 hours after implantation of the leukemia cell. IP denotes intraperitoneal drug injection and IV denotes intravenous. Doxorubicin hydrochloride was administered for comparison.

Nine mice were employed in each test. The animals were observed and their survival compared with that of control animals which received the same tumor inoculation but were not treated with drug. The results are shown in Table 1 where T/C is the ratio of the median survival time of the treated animals divided by the median survival time of the control animals. An increase in the T/C indicates an increase in the antitumor activity of the compound. If T/C is less than 100, the compound is considered toxic. For example in the first study shown in the Table, Compound 1 is not toxic up to 50 mg/kg whereas Doxorubicin is toxic at 12.5 mg/kg.

TEST COMPOUNDS

| Compound No. | Identification |
| --- | --- |
| 1 | 14-O—Acetyl-7-O—(3,4-di-O—acetyl-2,6-dideoxy-2-iodo-L-manno-hexopyranosyl adriamycinone |
| 2 | 14-O—Acetyl-7-O—(3,4-di-O—acetyl-2-bromo-2,6-dideoxy-α-L-talo-hexopyranosyl)adriamycinone |
| 3 | 14-O—Acetyl-7-O—(3,4-di-O—acetyl-2,6-dideoxy-2-iodo-α-L-talo-hexopyranosyl) adriamycinone |
| 4 | 14-O—Acetyl-7-O—(3,4-di-O—acetyl-2-bromo-2,6-dideoxy-α-L-manno-hexopyranosyl) adriamycinone |
| 5 | 14-O—Acetyl-7-O—(3,4-di-O—acetyl-2-chloro-2,6-dideoxy-α-L-manno-hexopyranosyl)-adriamycinone |
| 6 | 7-O—(3,4-Di-O—acetyl-2,6-dideoxy-2-iodo-α-L-manno-hexopyranosyl)-14-O—(5-carboxypentanoyl)adriamycinone |

TABLE 1

| Tumor System | Test Compound No. | Route | Schedule | Dose (mg/kg) | T/C |
| --- | --- | --- | --- | --- | --- |
| P388 | 1 | IP | Day 1 | 50 | 54 |
| | | | | 25 | >300 |
| | | | | 12.5 | 181 |
| | | | | 6.25 | 152 |
| | | | | 3.12 | 142 |
| | | | | 1.56 | 111 |
| | Doxorubicin | | | 12.5 | 98 |
| | | | | 6.25 | 206 |
| P388 | 1 | IV | Day 1 | 20 | 156 |
| | | | | 15 | 141 |
| | | | | 10 | 136 |
| | | | | 5 | 120 |
| | Doxorubicin | | | 15 | 199 |
| L1210 | 1 | IP | Days 1,5,9 | 15 | 234 |
| | | | | 7.5 | 176 |
| | | | | 3.75 | 141 |
| | | | | 1.88 | 129 |
| | Doxorubicin | | | 3 | 158 |
| | | | | 2 | 148 |
| B16 | 1 | IP | Day 1 | 50 | 54 |
| | | | | 37.5 | 226 |
| | | | | 25 | 209 |
| | | | | 12.5 | 172 |
| | Doxorubicin | | | 10 | >293 |
| P388 | 2 | IP | Day 1 | 25 | 204 |
| | | | | 12.5 | 150 |
| | | | | 6.25 | 138 |
| | | | | 3.12 | 117 |
| | Doxorubicin | | | 6.25 | 209 |
| B16 | 2 | IP | Day 1 | 50 | 203 |
| | | | | 25 | 146 |
| | | | | 12.5 | 160 |
| | | | | 6.25 | 123 |
| | Doxorubicin | | | 20 | >268 |
| P388 | 3 | IP | Day 1 | 25 | 172 |
| | | | | 12.5 | 147 |
| | | | | 6.25 | 126 |
| | | | | 3.12 | 114 |
| | Doxorubicin | | | 6.25 | 209 |
| P388 | 4 | IP | Day 1 | 50 | 318 |
| | | | | 25 | 238 |
| | | | | 12.5 | 218 |
| | | | | 6.25 | 172 |
| | | | | 3.12 | 147 |
| | Doxorubicin | | | 6.25 | 209 |
| L1210 | 4 | IP | Days 1,5,9 | 15 | 234 |
| | | | | 7.5 | 171 |
| | | | | 3.75 | 141 |
| | | | | 1.88 | 127 |
| | Doxorubicin | | | 4 | 158 |
| B16 | 4 | IP | Day 1 | 25 | 239 |
| | | | | 12.5 | 151 |
| | | | | 6.25 | 148 |
| | | | | 3.12 | 130 |
| | Doxorubicin | | | 20 | >268 |
| P388 | 5 | IP | Day 1 | 25 | 254 |
| | | | | 12.5 | 249 |
| | | | | 6.25 | 195 |
| | | | | 3.12 | 173 |
| | Doxorubicin | | | 5 | 276 |
| L1210 | 6 | IP | Days 1,5,9 | 15 | 342 |
| | | | | 7.5 | 184 |
| | | | | 3.75 | 138 |
| | | | | 1.88 | 120 |
| | Doxorubicin | | | 4 | 158 |
| B16 | 6 | IP | Day 1 | 30 | 166 |
| | | | | 15 | 129 |
| | | | | 7.5 | 124 |
| | Doxorubicin | | | 10 | >234 |

BIOLOGICAL EXAMPLE 2

Biological studies conducted using selected 14-acyloxy-2'-anthracyclines indicate that administration of 14-O-acetyl-7-O-(3,4-di-O-acetyl-2,6-dideoxy-2-iodi-α-L-manno-hexopyranosyl) adriamycinone (Compound 1) produces no evidence of cardiotoxicity when compared to the administration of similar regimens of doxorubicin hydrochloride in mice. Intradermal administration of Compound 1 failed to cause extravasation (development of skin ulcers). Intradermal administration of 7-O-(3,4-di-O-acetyl-2,6-dideoxy-2-iodo-α-L-manno-hexopyranosyl)-14-O-(5-carboxypentanoyl)adriamycinone (Compound 6) was responsible for substantially fewer lesions in comparison to those noted in animals administered doxorubicin hydrochloride.

Experimental

Extravasation Study

Groups of either mice or rats (10/group) were injected intradermally with 0.1 ml of Compound 1 suspended in cremaphor at concentrations of 2 mg/ml or Compound 6 suspended in saline at concentrations of 2 mg/ml and 1 mg/ml. Similar groups were given doxorubicin hydrochloride at identical concentrations as a positive control. The animals were observed frequently for lesions. The results are shown in Table 2.

TABLE 2

| | | Number of Animals with Lesions | | | | |
|---|---|---|---|---|---|---|
| | Dosage | Day 5 | Day 9 | Day 11 | Day 14 | Day 21 |
| MOUSE EXTRAVASATION | | | | | | |
| Compound 1 | .1 ml (2 mg/ml) | 0/10 | 0/10 | 0/10 | 0/10 | 0/10 |
| Doxorubicin | .1 ml (2 mg/ml) | 10/10 | 10/10 | 10/10 | 10/10 | 10/10 |
| Cremophor (Control) | .1 ml | 0/10 | 0/10 | 0/10 | 0/10 | 0/10 |
| RAT EXTRAVASATION | | | | | | |
| Compound 6 | .1 ml (2 mg/ml) | 2/10 | 1/10 | 1/10 | 0/10 | 0/10 |
| Doxorubicin | .1 ml (2 mg/ml) | 6/10 | 9/10 | 9/10 | 8/10 | 8/10 |
| Compound 6 | .1 ml (1 mg/ml) | 1/10 | 0/10 | 0/10 | 0/10 | 0/10 |
| Doxorubicin | .1 ml (1 mg/ml) | 8/10 | 10/10 | 10/10 | 10/10 | 10/10 |
| Saline Control | .1 ml | 0/10 | 0/10 | 0/10 | 0/10 | 0/10 |

Cardiotoxicity Study

Groups of 12 Cox ICR Swiss mice each were given 10 injections of Compound 1 at dosages of 3,6 or 8 mg/kg/inj according to a published experimental protocol described by Bertazzoli et al. (Cancer Treatment Reports 63:1877, 1979). The animals were sacrificed at 11 weeks. Hearts were removed and fixed in paraformaldehyde, embedded in acrylic plastic and sectioned for histologic examination by a certified veterinary pathologist, who examined each heart for vacuolar degeneration and graded the lesions according to severity (Grade 1=mild; Grade 4=severe). The results are shown in Table 3.

TABLE 3

| Drug Treatment | Dose (mg/kg/inj) | No. of Mice with Cardiac Lesions | | | | No. of Normals | Total Examined |
|---|---|---|---|---|---|---|---|
| | | Gr. 1 | Gr. 2 | Gr. 3 | Gr. 4 | | |
| Doxorubicin | 3 | 3 | 3 | 0 | 0 | 6 | 12 |
| Doxorubicin | 4 | 5 | 4 | 2 | 0 | 0 | 12 |
| Doxorubicin | 5 | 2 | 2 | 6 | 2 | 0 | 12 |
| Compound 1 | 4 | 0 | 0 | 0 | 0 | 12 | 12 |
| Compound 1 | 6 | 0 | 0 | 0 | 0 | 12 | 12 |
| Compound 1 | 8 | 0 | 0 | 0 | 0 | 12 | 12 |

We claim:

1. A compound of the formula I

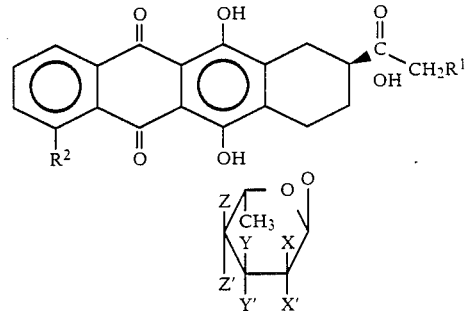

wherein $R^1$ is —OOCR$^3$ [or —OOC(CH$_2$)$_n$COOR$^4$]; $R^2$ is hydrogen, hydroxy or methoxy; one of X and X' is a halogen atom selected from the group consisting of fluorine, chlorine, bromine and iodine and the other is hydrogen; one of Y and Y' is hydrogen and the other is selected from the group consisting of hydrogen, hydroxy and acyloxy; one of Z and Z' is hydrogen and the other is selected from the group consisting of hydrogen, hydroxy and acyloxy; and $R^3$ is an alkyl group containing 1 to 8 carbon atoms; and pharmaceutically acceptable salts thereof.

2. The compound of claim 1 wherein X' is bromine or iodine.

3. The compound of claim 2 wherein X' is bromine or iodine, Y' is acetoxy or hydroxy and Z is acetoxy or hydroxy.

4. A pharmaceutical preparation comprising a therapeutically effective amount of a compound of the formula (I)

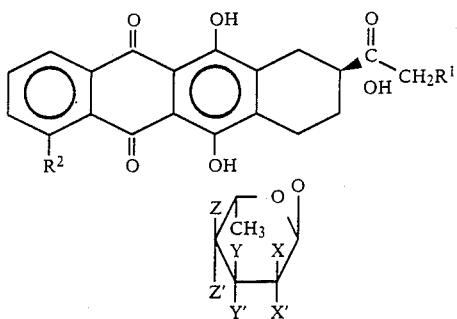

wherein $R^1$ is $-OOCR^3$; $R^2$ is hydrogen, hydroxy or methoxy; one of X and X' is a halogen atom selected from the group consisting of fluorine, chlorine, bromine and iodine and the other is hydrogen; and one of Y and Y' is hydrogen and the other is selected from the group consisting of hydrogen, hydroxy and acyloxy; one of Z and Z' is hydrogen and the other is selected from the group consisting of hydrogen, hydroxy and acyloxy; and $R^3$ is an alkyl group containing 1 to 8 carbon atoms; in combination with a pharmaceutically acceptable carrier.

5. The pharmaceutical preparation of claim 4 wherein X' is bromine or iodine.

6. The pharmaceutical preparation of claim 5 wherein X' is bromine or iodine, Y' is acetoxy or hydroxy and Z is acetoxy or hydroxy.

* * * * *